United States Patent [19]
Turnbull

[11] Patent Number: 5,647,344
[45] Date of Patent: Jul. 15, 1997

[54] HEAT AND MOISTURE EXCHANGERS

[75] Inventor: Christopher Stratton Turnbull, Hythe, England

[73] Assignee: Smiths Industries PLC, London, England

[21] Appl. No.: 662,316

[22] Filed: Jun. 13, 1996

[30]    Foreign Application Priority Data

Jul. 15, 1995 [GB] United Kingdom ............... 9514527

[51] Int. Cl.⁶ .................................................. A61M 15/00
[52] U.S. Cl. ........................... 128/201.13; 128/204.13; 128/204.17; 128/205.12; 604/406
[58] Field of Search ................ 128/201.13, 204.17, 128/203.26, 203.27, 204.15, 204.13, 206.16, 206.17, 719, 205.12, 205.27; 165/140, 141, DIG. 9, DIG. 10; 604/406; 95/52

[56]             References Cited

U.S. PATENT DOCUMENTS

| 4,327,717 | 5/1982 | Oetjen et al. ................... 128/201.13 |
| 4,612,019 | 9/1986 | Langhorst ................................... 95/52 |
| 4,840,227 | 6/1989 | Schmidt ................................... 165/162 |
| 5,067,971 | 11/1991 | Bikson et al. ............................. 55/16 |
| 5,282,964 | 2/1994 | Young et al. ......................... 210/321.8 |

FOREIGN PATENT DOCUMENTS

| 1131524 | 9/1982 | Canada ............................. 128/201.13 |
| 0 009 543 | 4/1980 | European Pat. Off. ........ A61M 16/00 |
| 0134326 | 2/1979 | Germany ..................... 128/205.27 |
| 2900484 | 8/1980 | Germany . |
| 2053694 | 2/1981 | United Kingdom .......... A61M 16/00 |
| 8904684 | 6/1989 | WIPO ............................... 128/204.17 |

*Primary Examiner*—Vincent Millin
*Assistant Examiner*—V. Srivastara
*Attorney, Agent, or Firm*—Pollock, Vande Sande & Priddy

[57]             ABSTRACT

An HME has an exchange element comprising a bundle of hollow fibers parallel to the direction of gas flow through the HME. The fibers are of a polymeric material, such as a sulphone, and are treated with a hygroscopic material. The bundle of fibers is held together by an outer sleeve and a porous cap at each end.

11 Claims, 1 Drawing Sheet

HEAT AND MOISTURE EXCHANGERS

BACKGROUND OF THE INVENTION

This invention relates to heat and moisture exchangers and breathing circuits including a heat and moisture exchanger.

Heat and moisture exchangers (HMEs) are used to warm and moisten gas supplied to a patient. The HME comprises a housing coupled in the patient breathing circuit, through which both inhaled and exhaled gas pass. Within the housing, an exchange element takes up a part of the heat and moisture in the expired gas and transfers a part of this to the inspired gas when flow is reversed. The exchange element may be a coiled strip of corrugated paper treated with a hygroscopic material or a foam. HMEs are sold by Portex Limited of Hythe, England under the trade mark Thermovent. Examples of HMEs are described in: GB 2277689; GB 2268496; GB2267840; EP 535016; EP 533644; EP 387220; EP 265163; EP 413127; U.S. Pat. No. 4,516,573; U.S. Pat. No. 4,090,513; U.S. Pat. No. 4,771,770; U.S. Pat. No. 4,200,094; and U.S. Pat. No. 4,048,993.

HMEs have the advantage over conventional humidifiers in that they can be compact, light, and disposable after a single use. The HME should preferably have a low resistance to flow, a high efficiency in exchange of heat and moisture, a long life and be easily made at low cost. The HME must also present no hazard to the patient.

BRIEF SUMMARY OF THE INVENTION

It is an object of the present invention to provide an improved HME.

According to one aspect of the present invention there is provided an HME having an exchange element within an outer casing, the casing having inlets at opposite ends of the exchange element such that gas flows through the exchange element in opposite directions when flow of gas to the HME is reversed, the exchange element including a bundle of hollow fibres arranged parallel to one another.

The fibres preferably have porous walls and are preferably arranged parallel to the direction of gas flow through the casing such that some at least of the gas flows along the bores of the fibres. The fibres may be treated with a hygroscopic material. The fibres are preferably of a polymeric material such as a sulphone. The bundle of fibres may have a porous cap at each end and may be held together by an outer sleeve. The fibres are preferably of circular section.

According to another aspect of the present invention there is provided a breathing circuit including an HME according to the above one aspect of the present invention.

An HME according to the present invention, will now be described, by way of example, with reference to the accompanying drawing.

DETAILED DESCRIPTION OF THE PREFERRED EMBODIMENTS

Figure 1:
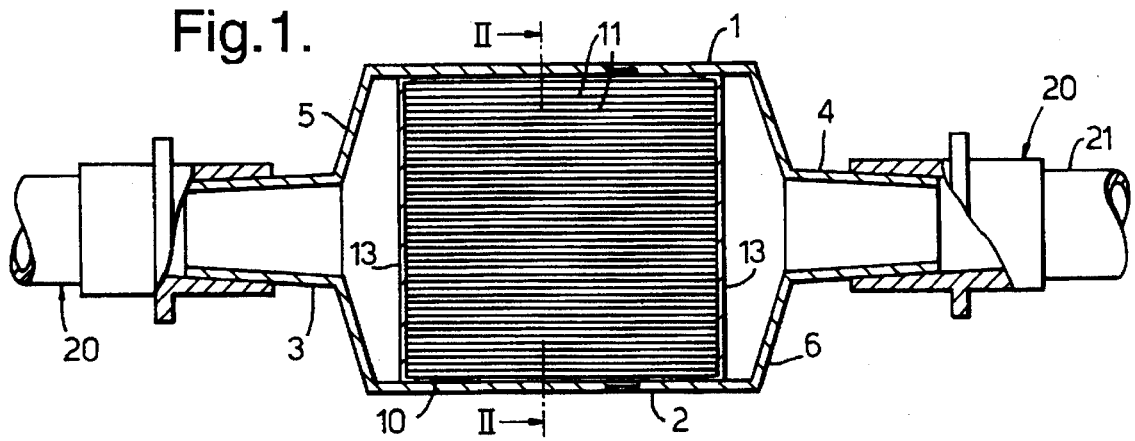
FIG. 1 is a partly sectional side elevation view of the HME.
Figure 2:
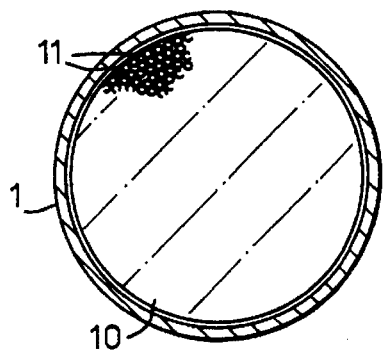
FIG. 2 is a cross-sectional view through the HME along the line II—II of FIG. 1.
Figure 3:
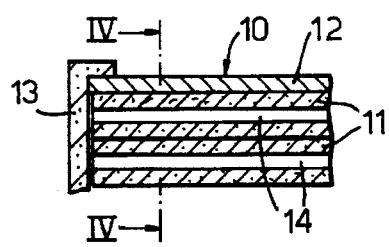
FIG. 3 is an enlarged sectional side elevation of a part of the HME.
Figure 4:
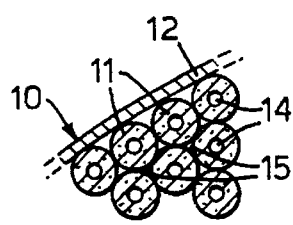
FIG. 4 is a cross-section along the line IV—IV of FIG. 3.

The HME has a conventional outer casing 1 of generally cylindrical shape made from a rigid, transparent plastics material, such as polycarbonate. The casing 1 has a central region 2 with a length and an external diameter of about 30 mm. At opposite ends, the casing 1 is formed with two inlets in the form of male, luer-tapered terminations 3 and 4 of reduced diameter, which are connected with the central region 2 by short frusto-conical shoulders 5 and 6 respectively. The casing is preferably made in two parts to enable installation of an exchange element 10 and could be reusable with single-use exchange elements.

The exchange element 10 is located within the central region 2 so that the inlets 3 and 4 are located at opposite ends of the element. The exchange element comprises a cylindrical bundle of hollow fibres 11 held together by a shrink-wrap sleeve 12, or some other means, around its circumference and by porous end caps 13. The fibres 11 are made from a sulphone, such as polysulphone or polyether sulphone, with an external diameter of between about 0.25 mm and 1.5 mm. The fibres are made by extruding a solvent-based solution of the polymer through an annular die into a water bath. The solvent comes out of solution into the water, leaving the polymer structure behind. This results in a porous wall structure of the fibres, which allows gas to seep through the walls. The pore structure of the fibres can be varied by using different solvents, temperature and other extrusion factors. There are various other ways in which the fibres could be made, such as, solution casting or a melt process.

The fibres 11 in the bundle are aligned parallel with one another and longitudinally of the casing 1, parallel with its axis, so that they are parallel to the flow of gas through the HME. The fibres 11 are preferably treated with a hygroscopic material, such as calcium chloride, to increase their ability to retain water. This treatment may be accomplished by immersing the bundle in a solution of calcium chloride and then drying to leave crystals of the calcium chloride. Alternatively, the fibres could be treated during their manufacture, rather than after bundling together. The porous structure of the walls of the fibres can help hold calcium chloride crystals on the inside and outside surfaces.

The HME is connected in a patient breathing circuit 20 so that gas supplied to and from the patient must flow through the HME. The circuit includes a tracheal tube 21, mask or the like through which gas is supplied to and from the patient. Gas flows through the bundle of fibres, both along the bores 14 of the fibres and along their outside, through the gaps 15 between adjacent fibres. A small amount of gas may also flow through the walls of the fibres. The fibres shown have a circular section but they could have other shapes, such as hexagonal, to vary the packing of the fibres and the gas flow characteristics along the HME. Exhaled gas warms and moistens the fibre bundle. Inhaled gas passing through the element 10 in the opposite direction takes up moisture and heat from the bundle so that the cold dry gas supplied to the breathing circuit 20 is warmed and moistened before it is inhaled by the patient.

The hollow-fibre bundle exchange element 10 has a large surface area exposed to gas flow, making the exchange element very efficient. The surface of the fibres can be easily modified chemically to vary the properties of the exchange element. The porous nature of the fibre walls increases gas turbulence and may enable a high retention of hygroscopic material, both of which help improve the efficiency of the HME.

It will be appreciated that various different materials could be used for the fibres.

What I claim is:

1. An HME comprising: an outer casing; two inlets on the casing spaced from one another; and an exchange element within said casing, said element being located between said inlets such that gas flows through the exchange element in opposite directions when flow of gas to the HME is reversed, wherein said exchange element is provided by a bundle of hollow fibres arranged parallel to one another, and wherein said fibres are arranged such that gas flows through said bundle in both directions both along the bores of said fibres and along spaces between the fibres.

2. An HME according to claim 1, wherein said fibers have porous walls.

3. An HME according to claim 1, wherein said fibers are treated with a hygroscopic material.

4. An HME according to claim 1, wherein said fibers are of a polymeric material.

5. An HME according to claim 4, wherein said fibers are of a sulfone.

6. An HME according to claim 1, wherein the bundle of fibers has a porous cap at each end.

7. An HME according to claim 1, wherein the bundle of fibers is held together by an outer sleeve.

8. An HME according to claim 1, wherein the fibers are of circular section.

9. An HME comprising: an outer casing, two inlets on the casing spaced from one another; and an exchange element within said casing, said element being located between said inlets such that gas flows through the exchange element in opposite directions when flow of gas to the HME is reversed, wherein said exchange element is provided by a bundle of hollow fibres arranged parallel to one another, wherein said fibres are arranged longitudinally of the casing, wherein said fibres are of a porous, polymeric material treated with a hygroscopic material, and wherein said fibres are arranged such that gas flows through said bundle in both directions both along the bores of said fibres and along spaces between the fibres.

10. An HME comprising: an outer casing; two inlets on the casing spaced from one another; and an exchange element within said casing, said element being located between said inlets such that gas flows through the exchange element in opposite directions when flow of gas to the HME is reversed, wherein said exchange element is provided by a bundle of hollow fibres arranged parallel to one another, wherein said fibres are arranged longitudinally of the casing, wherein said fibres are held together by an outer sleeve and by porous end caps at each end of the bundle, and wherein said fibres are arranged such that gas flows through said bundle in both directions both along the bores of said fibres and along spaces between the fibres.

11. A patent breathing circuit comprising: a tube through which gas can be supplied to and from a patient; and an HME, said HME comprising an outer casing, two inlets on the casing spaced from one another, and an exchange element within said casing, said element being located between said inlets such that gas flows through the exchange element in opposite directions when flow of gas in the breathing circuit is reversed, and said exchange element being provided by a bundle of hollow fibres arranged parallel to one another, said fibres being arranged such that gas flows through said bundle in both directions both along the bores of said fibres and along spaces between the fibres.

* * * * *